United States Patent
Zucker

(10) Patent No.: US 6,743,195 B2
(45) Date of Patent: Jun. 1, 2004

(54) BALLOON METHOD AND APPARATUS FOR VASCULAR CLOSURE FOLLOWING ARTERIAL CATHETERIZATION

(75) Inventor: Menachem Zucker, Kiryat Motzkin (IL)

(73) Assignee: Cardiodex, Tirat Hacarmel (IL)

( * ) Notice: Subject to any disclaimer, the term of this patent is extended or adjusted under 35 U.S.C. 154(b) by 0 days.

(21) Appl. No.: 09/808,630

(22) Filed: Mar. 14, 2001

(65) Prior Publication Data

US 2002/0133123 A1 Sep. 19, 2002

(51) Int. Cl.$^7$ .............................................. A61M 29/00
(52) U.S. Cl. .............................. 604/101.01; 604/96.01; 604/101.05
(58) Field of Search ............................ 604/246, 96.01, 604/99.02, 101.01, 101.03, 101.04, 101.05, 102.01, 102.02, 102.03, 164.01, 164.02, 164.03, 164.08, 164.09, 164.11, 164.13, 264, 30, 35; 606/213, 214, 215

(56) References Cited

U.S. PATENT DOCUMENTS

| | | | |
|---|---|---|---|
| 4,364,392 A | 12/1982 | Strother et al. ............. 128/325 |
| 4,744,364 A | * 5/1988 | Kensey ....................... 128/334 |
| 4,836,204 A | * 6/1989 | Landymore et al. ........ 128/334 |
| 5,217,024 A | 6/1993 | Dorsey et al. .............. 128/758 |
| 5,370,660 A | 12/1994 | Weinstein et al. .......... 606/215 |
| 5,413,571 A | 5/1995 | Katsaros et al. ............ 606/213 |
| 5,419,765 A | * 5/1995 | Weldon et al. ................ 604/96 |
| 5,458,573 A | * 10/1995 | Summers ..................... 604/101 |
| 5,486,195 A | 1/1996 | Myers et al. ................ 606/213 |
| 5,540,715 A | 7/1996 | Katsaros et al. ............ 606/213 |
| 5,645,566 A | 7/1997 | Brenneman et al. ........ 606/213 |
| 5,700,277 A | 12/1997 | Nash et al. .................. 606/213 |
| 5,725,551 A | 3/1998 | Myers et al. ................ 606/213 |
| 5,728,134 A | 3/1998 | Barak ......................... 606/214 |
| 5,853,421 A | 12/1998 | Leschinsky et al. ........ 606/213 |
| 5,928,266 A | 7/1999 | Kontos ........................ 606/213 |
| 6,022,336 A | * 2/2000 | Zadno-Azizi et al. ......... 604/96 |
| 6,048,358 A | 4/2000 | Barak ......................... 606/213 |
| 6,126,635 A | * 10/2000 | Simpson et al. ............ 604/101 |

FOREIGN PATENT DOCUMENTS

WO          WO 98/11830          3/1998

OTHER PUBLICATIONS

Overview of CompressAR. 2002.
Angio–Seal™. 2002.
The Prostar®, Perclose, Inc. 2002.
Silber, S. "Vascular Closure Devices for Immediate.." in Handbook of Coronary Stents, 3rd ed. (Martin Dunitz, 2000).
U.S. patent application Ser. No. 09/598,232 to Menachem Zucker, entitled Mechanical Method and Apparatus for Enhancing Hemostasis Following Arterial Catheterization, filed Jun. 21, 2000.

* cited by examiner

Primary Examiner—Long V. Le
Assistant Examiner—Ann Y. Lam
(74) Attorney, Agent, or Firm—Ladas & Parry

(57) ABSTRACT

Apparatus for hemostasis of an artery having a puncture after arterial catheterization, the apparatus includes a catheter introducer having a forward end and a hemostasis device including an elongate flexible hollow shaft having an inflatable anchor balloon at a forward end thereof and an inflatable peripheral balloon adjacent the forward end of the flexible hollow shaft, the hemostasis device being arranged to be insertable into an artery via the catheter introducer.

40 Claims, 13 Drawing Sheets

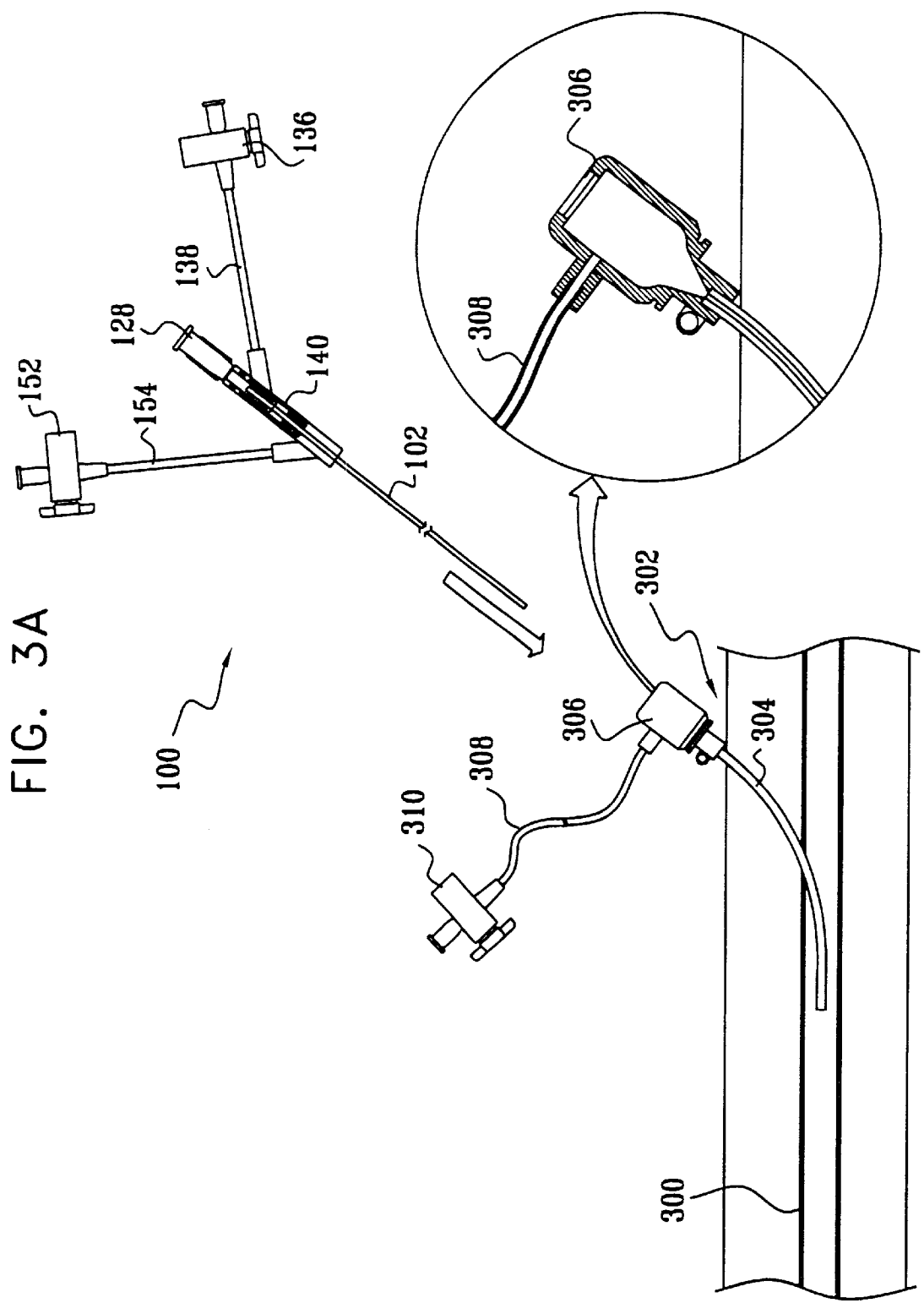

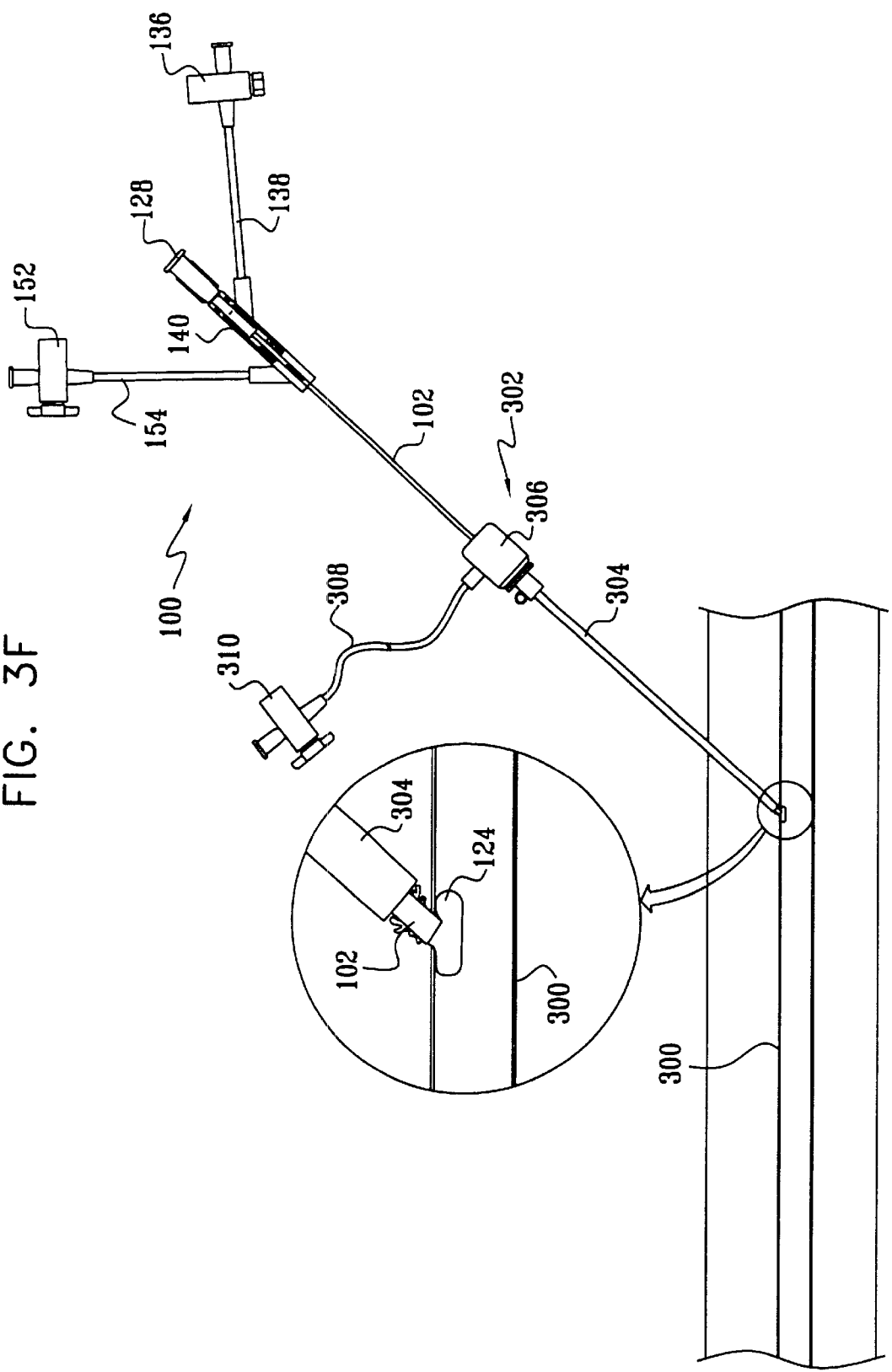

BALLOON METHOD AND APPARATUS FOR VASCULAR CLOSURE FOLLOWING ARTERIAL CATHETERIZATION

FIELD OF THE INVENTION

The present invention relates to catheterization systems and methodologies generally and more particularly to post-catheterization closure.

BACKGROUND OF THE INVENTION

Applicant's U.S. Pat. No. 5,728,134 and Published PCT Patent application WO 98/11830 describe a method and apparatus for hemostasis which greatly simplifies hemostasis and thus greatly reduces patient discomfort following arterial catheterization. The prior art referenced in Applicant's Published PCT Patent application WO 98/11830 and U.S. Pat. No. 5,728,134 is considered to represent the state of the art.

SUMMARY OF THE INVENTION

The present invention seeks to provide improved systems and methodologies for post-catheterization closure.

There is thus provided in accordance with a preferred embodiment of the present invention an apparatus for hemostasis of an artery having a puncture after arterial catheterization. The apparatus includes a catheter introducer having a forward end and a hemostasis device including an elongate flexible hollow shaft having an inflatable anchor balloon at a forward end thereof and an inflatable peripheral balloon adjacent the forward end of the flexible hollow shaft, the hemostasis device is arranged to be insertable into an artery via the catheter introducer.

There is provided in accordance with another preferred embodiment of the present invention an apparatus for hemostasis of an artery having a puncture after arterial catheterization. The apparatus is adapted for use with a catheter introducer having a forward end and includes a hemostasis device, an elongate flexible hollow shaft having an inflatable anchor balloon at a forward end thereof and an inflatable peripheral balloon adjacent the forward end of the flexible hollow shaft, the hemostasis device is arranged to be insertable into an artery via the catheter introducer.

Further in accordance with a preferred embodiment of the present invention the flexible hollow shaft includes a central bore.

Preferably, the flexible hollow shaft includes a wall having an asymmetric cross section, with a relatively thick cross sectional region and a relatively thin cross-sectional region. Typically, there is formed in the relatively thick cross sectional region, a peripheral bore which extends to a peripheral balloon inflation location exterior of the wall and communicates thereat with an interior of the peripheral balloon.

Still further in accordance with a preferred embodiment of the present invention the central bore extends to an anchor balloon inflation location communicating with an interior of the inflatable anchor balloon.

Additionally in accordance with a preferred embodiment of the present invention the anchor balloon and the central bore are configured such that when the anchor balloon is deflated it can be withdrawn into the central bore at the anchor balloon inflation location. Preferably, the anchor balloon is configured such that when it is inflated, it extends beyond the end of the flexible hollow shaft.

Further in accordance with a preferred embodiment of the present invention the apparatus for hemostasis also includes a rod which is displaceable longitudinally inside and along the central bore. The rod which extends through the flexible hollow shaft and terminates at a first end in a manually engageable handle portion. At a second end, the rod is typically attached to the anchor balloon.

Still further in accordance with a preferred embodiment of the present invention the rod includes a multistrand cable surrounded by a plastic cylindrical seal and is attached at an extreme end thereof to an inner surface of the anchor balloon.

Moreover in accordance with a preferred embodiment of the present invention the apparatus for hemostasis also includes a stopcock and associated conduit, communicating with an interior of a head element to which the flexible hollow shaft is fixed at a rearward end thereof.

Further in accordance with a preferred embodiment of the present invention the interior of the head element communicates with the central bore of the flexible hollow shaft and thus communicates with the interior of the anchor balloon at the anchor balloon inflation location.

Still further in accordance with a preferred embodiment of the present invention, the apparatus for hemostasis also includes a stopcock and associated conduit, communicating with an interior the peripheral bore and thus communicates with the interior of the peripheral balloon.

There is further provided in accordance with a preferred embodiment of the present invention, a method for hemostasis of an artery having a puncture after arterial catheterization the catheterization using a catheter introducer. The method includes the steps of:

inserting into an artery a catheter introducer having a forward end, following arterial catheterization and removal of a catheter from the catheter introducer, introducing into the artery via the catheter introducer, a hemostasis device, which includes an elongate flexible hollow shaft having an inflatable anchor balloon at a forward end thereof and an inflatable peripheral balloon adjacent the forward end.

inflating the inflatable anchor balloon inside the artery, causing the inflatable anchor balloon to assume an inflated state, retracting the hemostasis device relative to the catheter introducer, until the anchor balloon in the inflated state engages the forward end of the catheter introducer, retracting the hemostasis device and the catheter introducer until the anchor balloon in the inflated state sealingly engages an inner wall surface of a wall of the artery about the catheter introducer, thereafter retracting the catheter introducer such that the forward end thereof lies outside the wall of the artery, while the anchor balloon in the inflated state blocks blood flow from the artery, inflating the peripheral balloon adjacent the forward end of the catheter introducer as it lies outside an outer surface of the wall of the artery, thereby causing the peripheral balloon to assume an inflated state, deflating the inflatable anchor balloon, thereafter, withdrawing the forward end of the flexible hollow shaft from the artery, while the peripheral balloon seals a region outside the artery and surrounding an aperture in the artery through which the forward end of the flexible shaft was withdrawn, allowing hemostasis to occur thereat and following hemostasis, deflating of the peripheral balloon and removal of the hemostasis device from the patient.

Further in accordance with a preferred embodiment of the present invention the method also includes injecting a hemostatic agent via the hemostasis device to a location external of the artery.

Still further in accordance with a preferred embodiment of the present invention the step of inflating the peripheral balloon includes:

initially inflating the peripheral balloon and thereafter, further inflating the peripheral balloon sufficiently to cause the forward end of the flexible hollow shaft to be withdrawn completely from the wall of the artery and simultaneously to prevent blood flow from the artery through the artery wall.

BRIEF DESCRIPTION OF THE DRAWINGS

The present invention will be understood and appreciated more fully from the following detailed description, taken in conjunction with the drawings in which:

FIGS. 3A–3L are simplified illustrations of a preferred mode of operation of the apparatus of FIGS. 1, 2A and 2B.

DETAILED DESCRIPTION OF PREFERRED EMBODIMENTS

Figures 1, 2A, 2B:
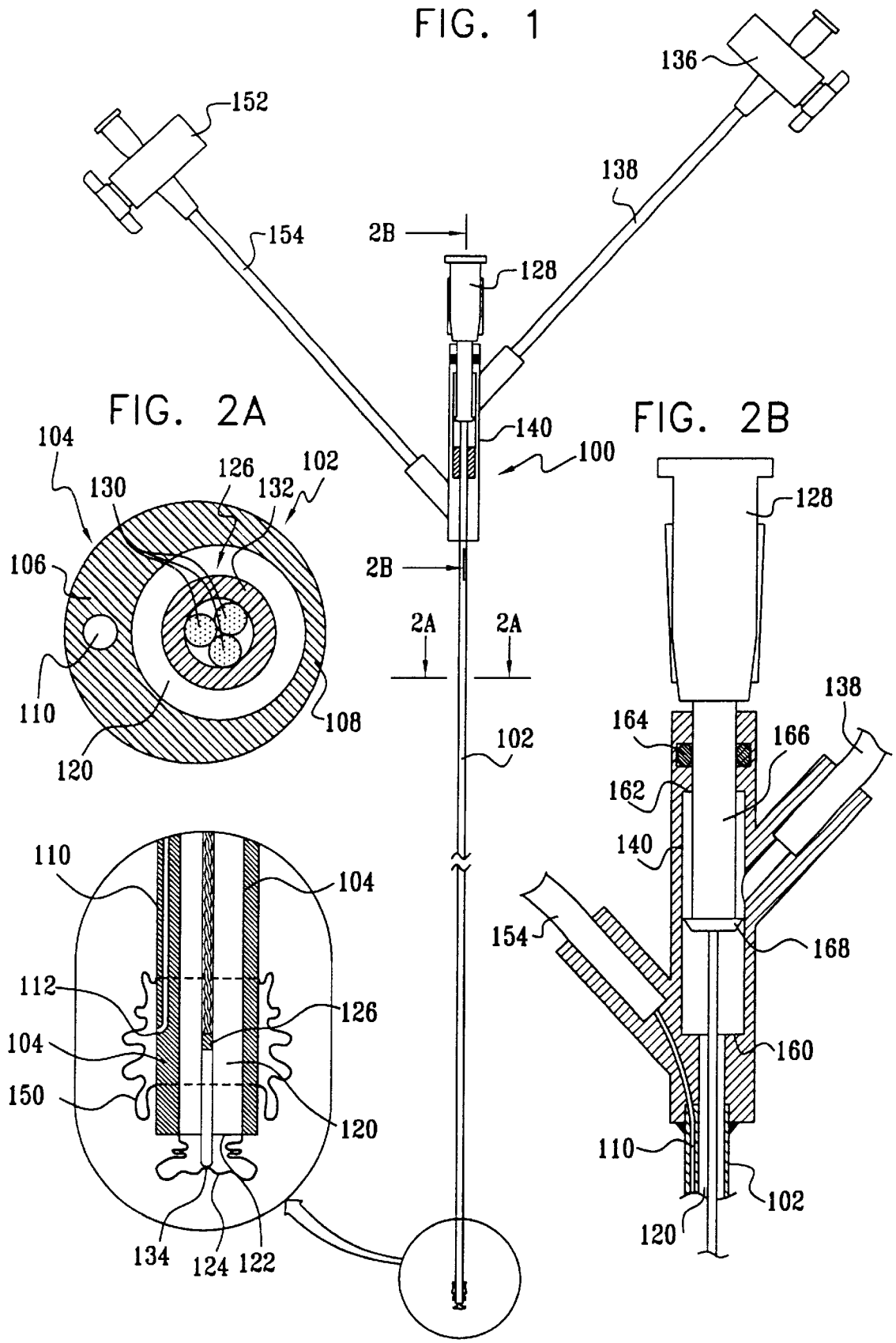
FIG. 1 is a simplified illustration of post catheterization closure apparatus constructed and operative in accordance with a preferred embodiment of the present invention.
FIGS. 2A and 2B are sectional illustrations, taken along lines 2A—2A and 2B—2B of FIG. 1.

Reference is now made to FIGS. 1, 2A and 2B, which are simplified illustrations of a hemostasis device 100 for producing hemostasis following arterial catheterization, in accordance with a preferred embodiment of the present invention. The hemostasis device 100 is suitable for insertion via a conventional catheter introducer (not shown) following completion of catheterization and removal of the catheter from the catheter introducer.

In accordance with a preferred embodiment of the present invention hemostasis device 100 comprises a main shaft 102, which preferably has an asymmetric wall 104, typically as shown in FIG. 2A, having a relatively thick region, designated generally by reference numeral 106 and a relatively thin region, designated generally by reference numeral 108. Extending along the wall 104 of the main shaft 102 at the relatively thick region there is preferably formed a bore 110 which extends to an peripheral balloon inflation location 112 exterior of wall 104.

Surrounded by asymmetric wall 104 is a central bore 120 which terminates at an anchor balloon inflation location 122.

Disposed at an end of main shaft 102 at anchor balloon inflation location 122 is an anchor balloon 124. It is a particular feature of the present invention that anchor balloon 124 is able to be withdrawn within bore 120 when deflated and extends beyond the end of main shaft 102 when inflated. Withdrawal of the anchor balloon, when deflated, into the end of central bore 120 adjacent inflation location 122 is preferably assisted by a rod 126 which is displaceable longitudinally inside and along bore 120 and which extends through main shaft 102 and terminates in a manually engageable handle portion 128. Rod 126 preferably comprises a multistrand cable 130 surrounded by a plastic cylindrical seal 132 and is attached at an extreme end thereof, designated by reference numeral 134 to an inner surface of balloon 124.

Anchor balloon 124 is selectably inflated via a stopcock 136 and associated conduit 138, communicating with the interior of a head element 140 to which main shaft 102 is fixed at an end thereof opposite to the end at which balloon 124 is located. The interior of head element 140 communicates with central bore 120 in main shaft 102, which in turn communicates with the interior of the anchor balloon 124 at anchor balloon inflation location 122.

Disposed adjacent the end of bore 110 in communication with peripheral balloon inflation location 112, exterior of wall 104 is a peripheral balloon 150, which is selectably inflated via bore 110, as via a stopcock 152 and associated conduit 154 which communicates with bore 110 via head element 140 as seen in FIG. 1.

It is noted that the head element 140 preferably defines interior travel stop surfaces 160 and 162 as well as an interior seal 164. Interior seal 164 sealingly engages a handle shaft 166 which is fixed to handle portion 128. Handle shaft 166 is preferably formed with a peripheral travel stop engagement protrusion 168 which is adapted to engage stop surfaces 160 and 162 when the handle portion 128 and thus rod 126 fixed thereto, is respectively fully extended or fully retracted.

Reference is now made to FIGS. 3A–3L, which illustrate various steps in a preferred mode of operation of the apparatus of FIGS. 1, 2A and 2B.

FIG. 3A illustrates the hemostasis device 100 about to be inserted into an artery 300 via a conventional catheter introducer assembly 302, following completion of a catheterization procedure and withdrawal of a catheter (not shown) from the catheter introducer assembly 302. The catheter introducer assembly 302 conventionally includes a sheath 304 and a conventional hemostasis valve 306 to which is coupled a substance introduction conduit 308 having a control valve 310.

Figure 3B:
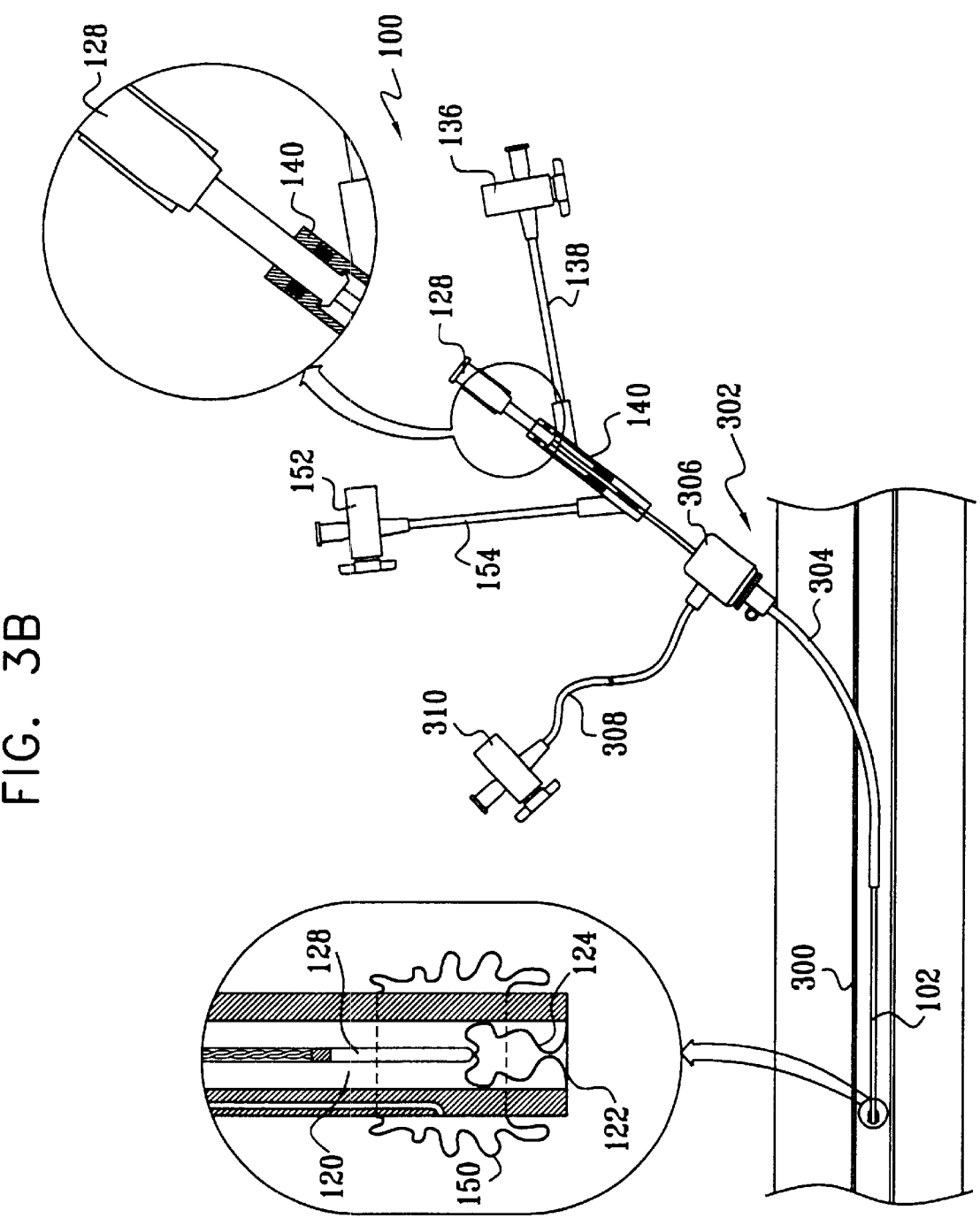

FIG. 3B shows the hemostasis device 100 inserted into the catheter introducer assembly 302 such that the outer end of the main shaft 102 extends into the artery 300 well beyond the end of catheter introducer sheath 304. As shown with particularity in FIG. 3B, at this stage both anchor balloon 124 and peripheral balloon 150 are deflated. and anchor balloon 124 is preferably fully retracted inside central bore 120 upstream of anchor balloon inflation location 122, by full retraction of handle portion 128 rearwardly of head element 140.

Figure 3C:
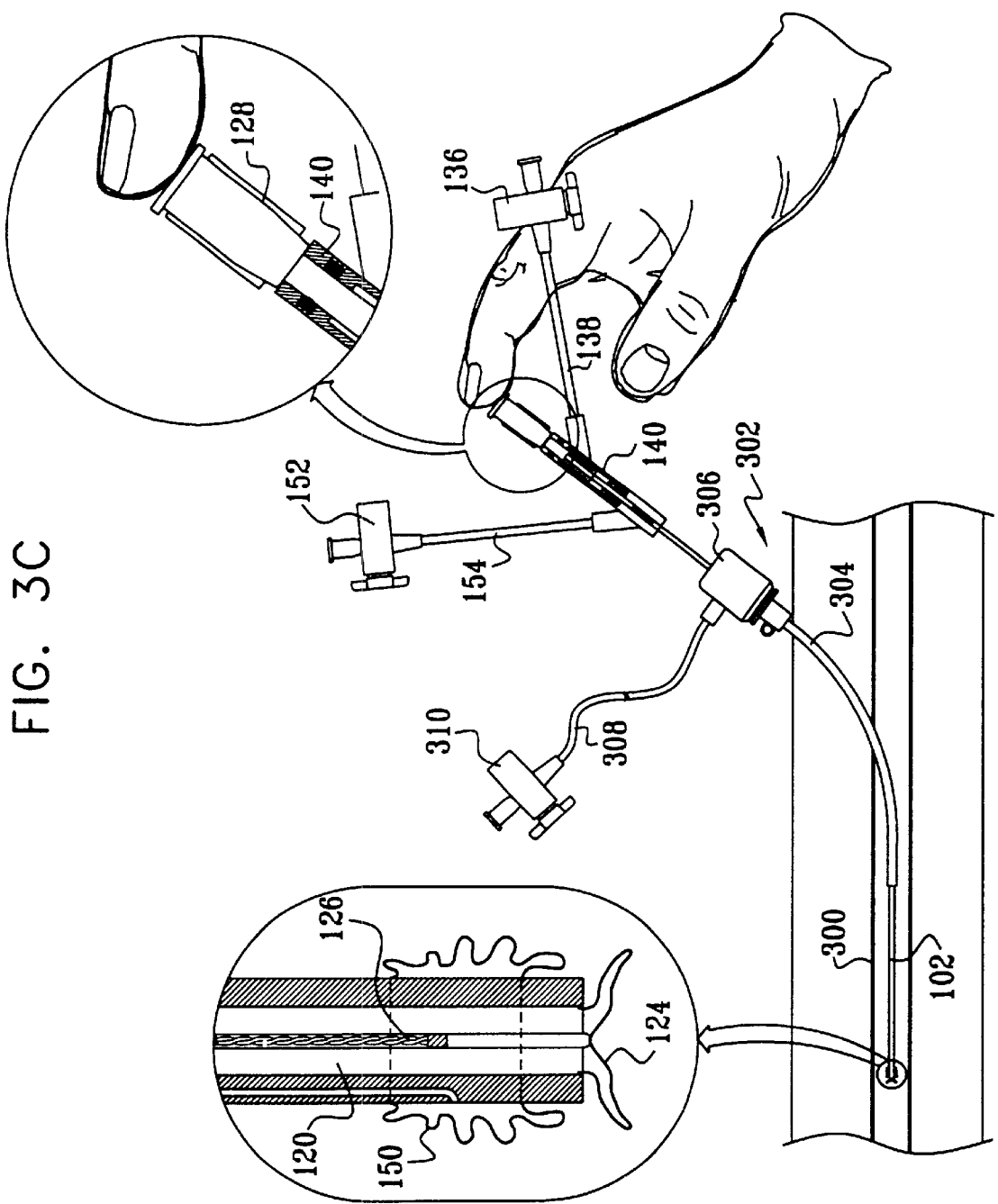

Reference is now made to FIG. 3C, which shows initial extension of anchor balloon 124 outside of central bore 120 by extension of handle portion 128 into engagement with head element 140. At this stage, both balloons 124 and 150 remain deflated.

Figure 3D:
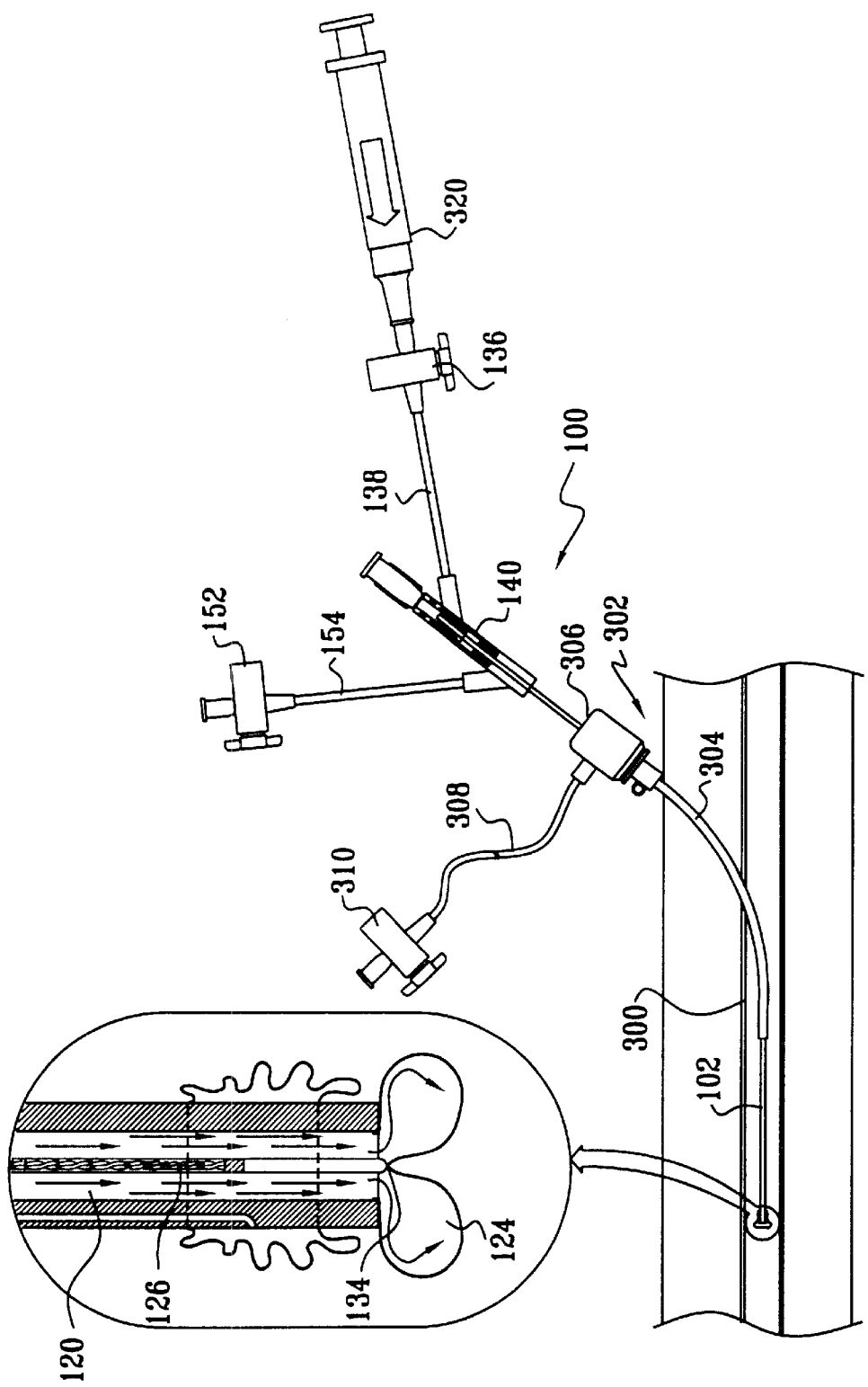

FIG. 3D illustrates initial inflation of the anchor balloon 124, preferably by use of a syringe 320 communicating with central bore 120 via the interior of head element 140, stopcock 136 and associated conduit 138 (FIG. 1). Due to the engagement of extreme end 134 of rod 126 with an inner surface of balloon 124, the inflated balloon preferably has a cusp-type configuration as seen with particularity in FIG. 3D.

This cusp-type configuration is associated with a particular feature of the present invention inasmuch as it provides pivotable mounting of the balloon 124 relative to main shaft 102, thereby to enable the anchor balloon 124 to sealingly align itself with the interior wall of artery 300 notwithstanding that the shaft 102 is normally not aligned perpendicularly thereto, as seen in the drawings.

Figure 3E:
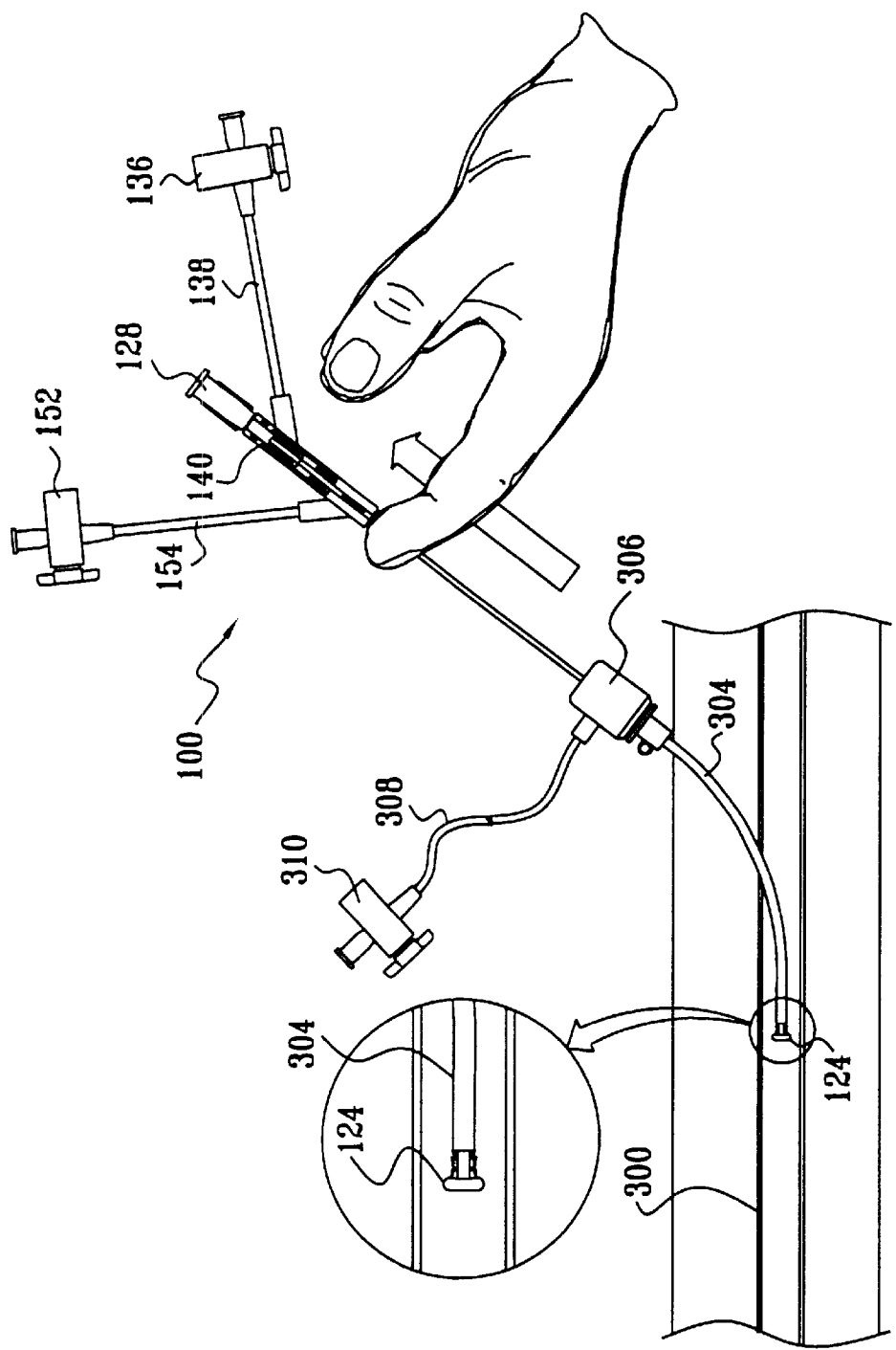

Following inflation of the anchor balloon 124, the hemostasis device 100 is partially retracted such that the inflated anchor balloon 124 rests tightly against the extreme end of the catheter introducer sheath 304, as seen in FIG. 3E.

Thereafter, the catheter introducer assembly 302 and the hemostasis device 100 are withdrawn together, such that the catheter introducer sheath 304 is removed from artery 300 only when the anchor balloon 124 already engages the interior wall of artery 300 in sealing engagement with the aperture in the artery 300 through which the catheter introducer shaft 304 is drawn and through which the main shaft 102 presently extends. This stage is shown in FIG. 3F.

Figure 3G:
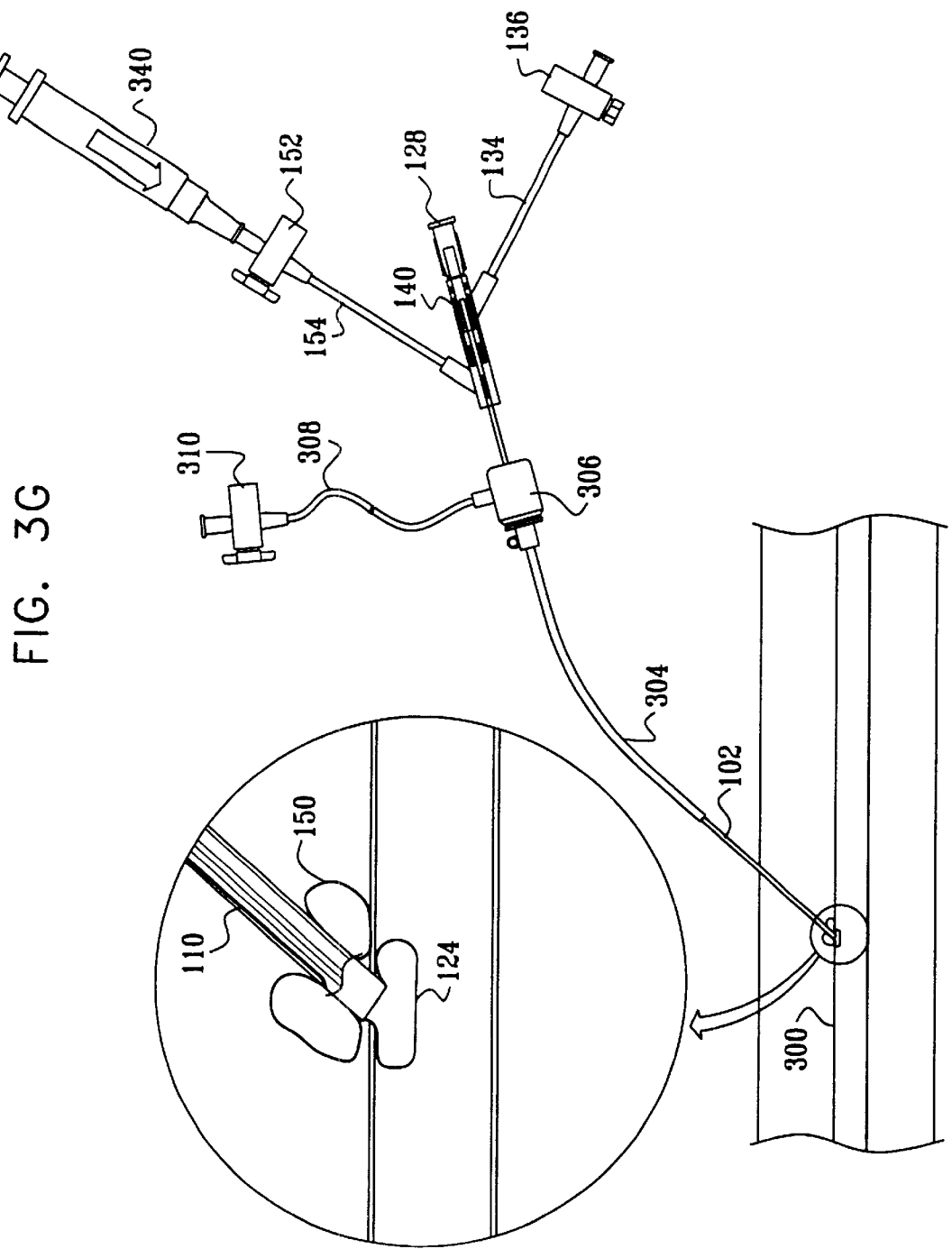
Figure 3H:
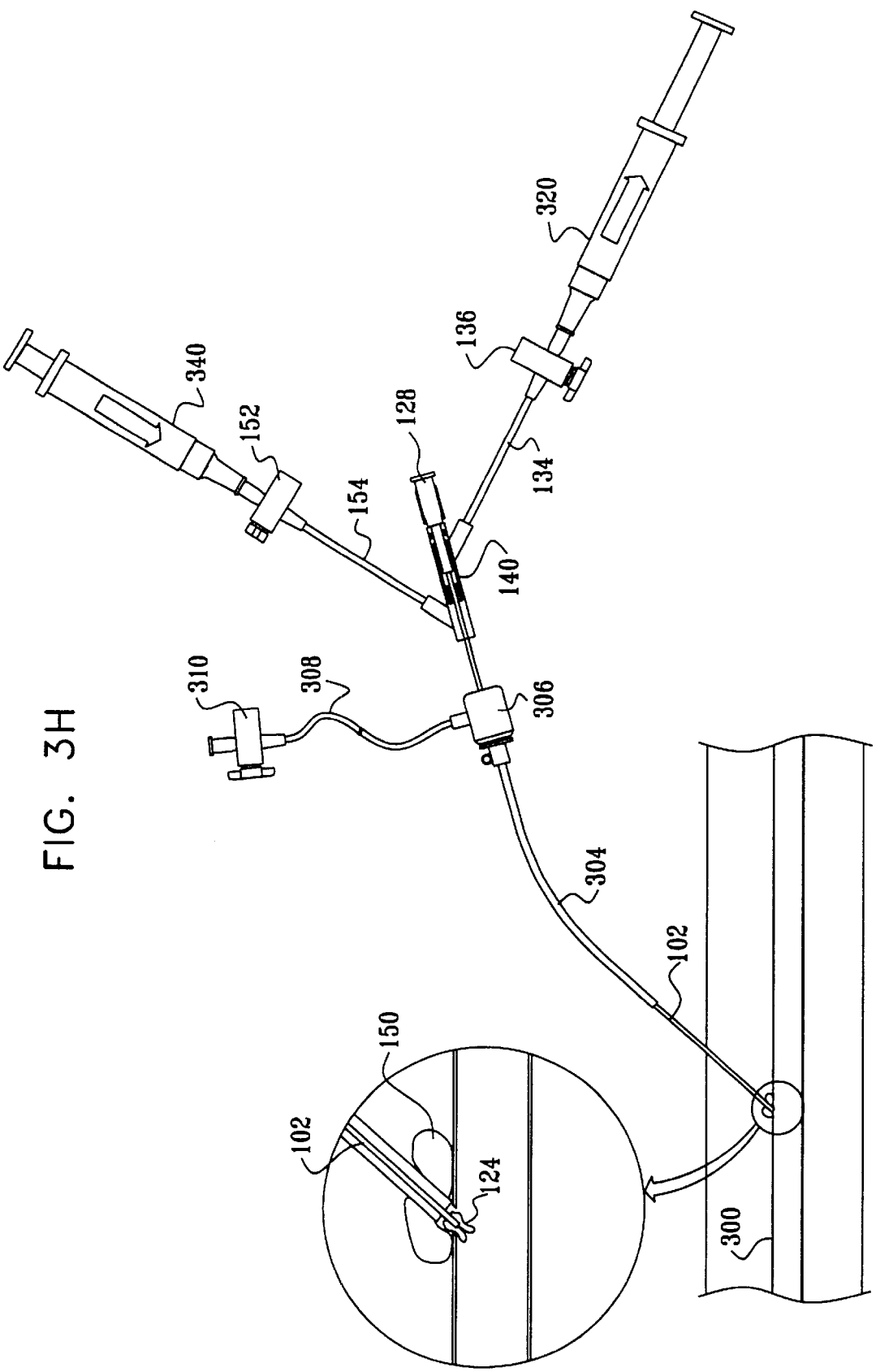

As seen in FIG. 3G, initial inflation of the peripheral balloon 150 is effected, preferably by use of a syringe 340 communicating with bore 110 via head element 140. stopcock 152 and associated conduit 154. Thereafter, as seen in FIG. 3H, the anchor balloon 124 is deflated and the peripheral balloon 150 is more fully inflated, which preferably causes the extreme end of the main shaft 102 to be withdrawn from the artery 300 to a location lying just outside the artery wall.

Figure 3I:
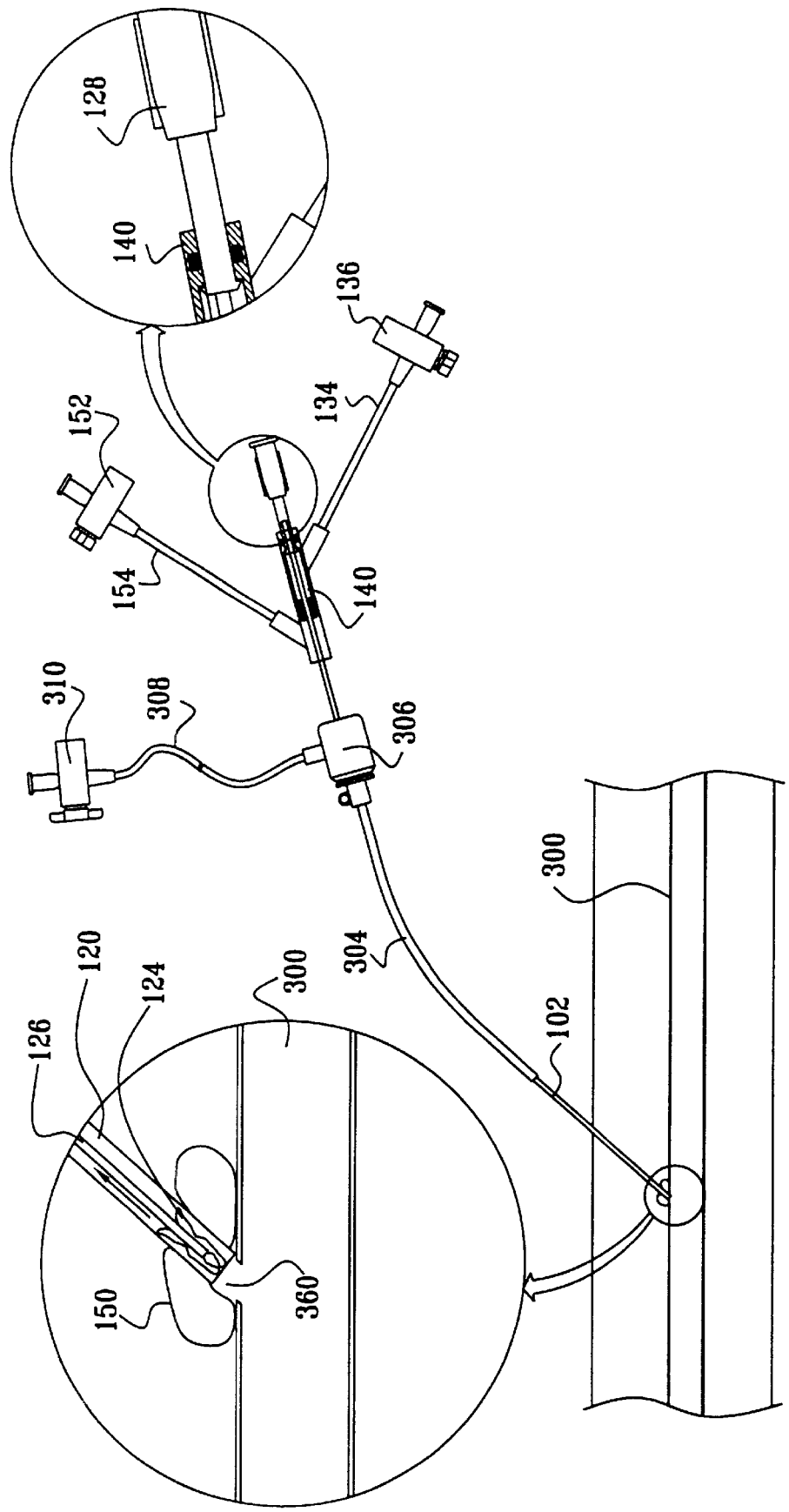
Figure 3J:
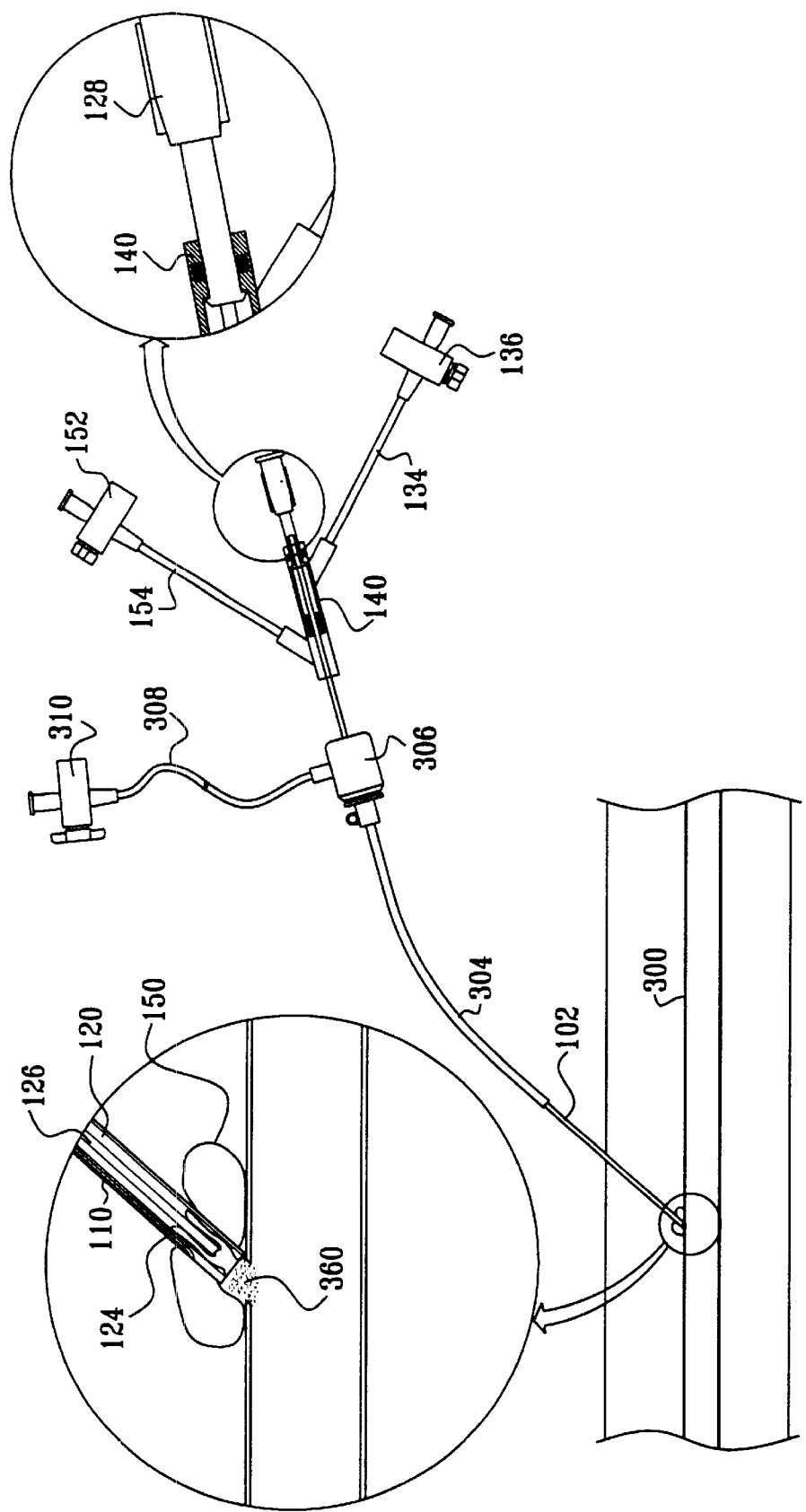

As shown in FIG. 3I, the deflated anchor balloon 124 is then retracted within the central bore 120, by full retraction of handle portion 128, allowing for hemostasis to take place in a region 360 outside of artery 300, which region is delimited by inflated peripheral balloon 150, as shown in FIG. 3J.

Figure 3K:
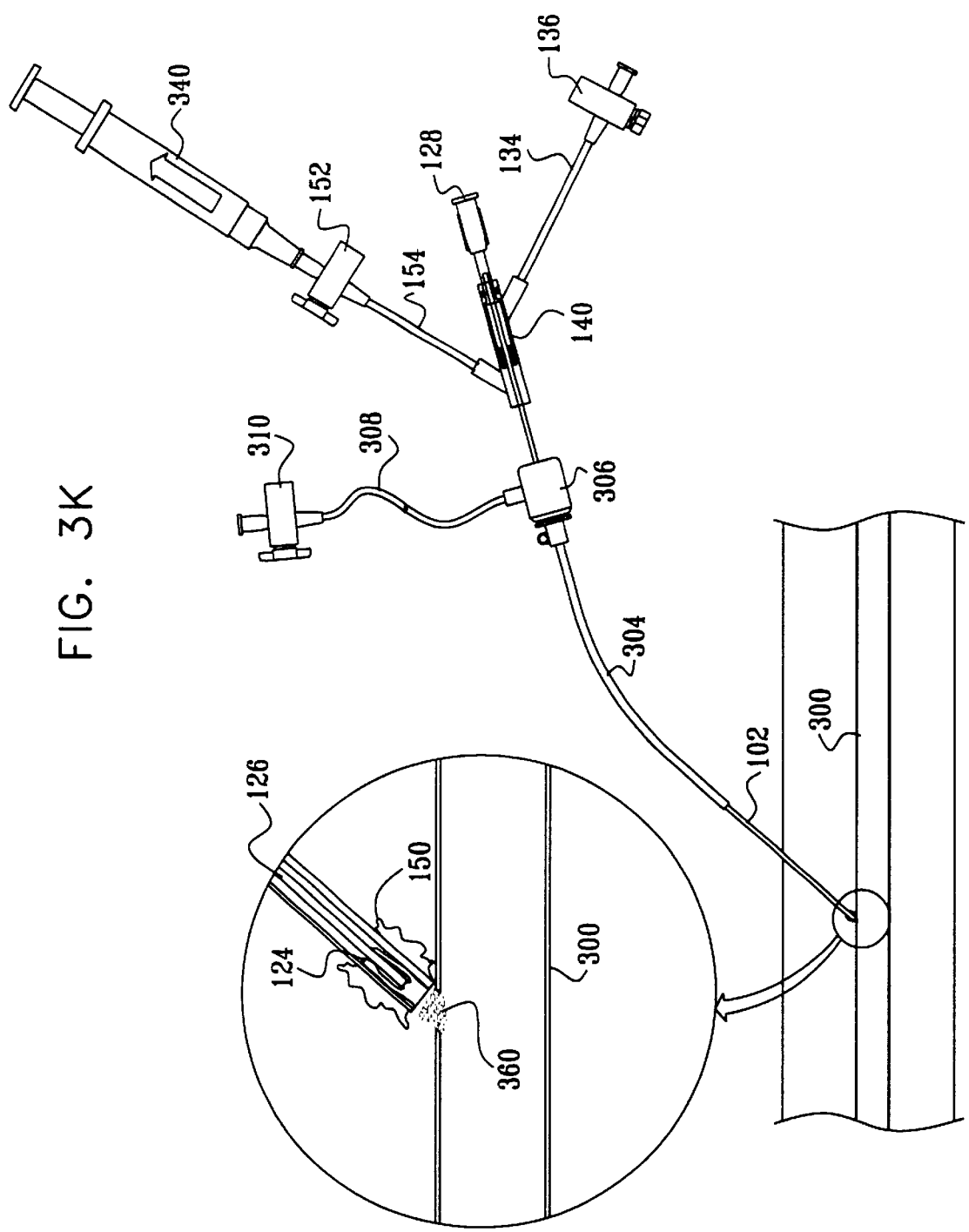

Once acceptable hemostasis has occurred in region 360, the peripheral balloon 150 is deflated, as shown in FIG. 3K, preferably by operation of syringe 340 communicating with bore 110 via head element 140, stopcock 152 and associated conduit 154.

Figure 3L:
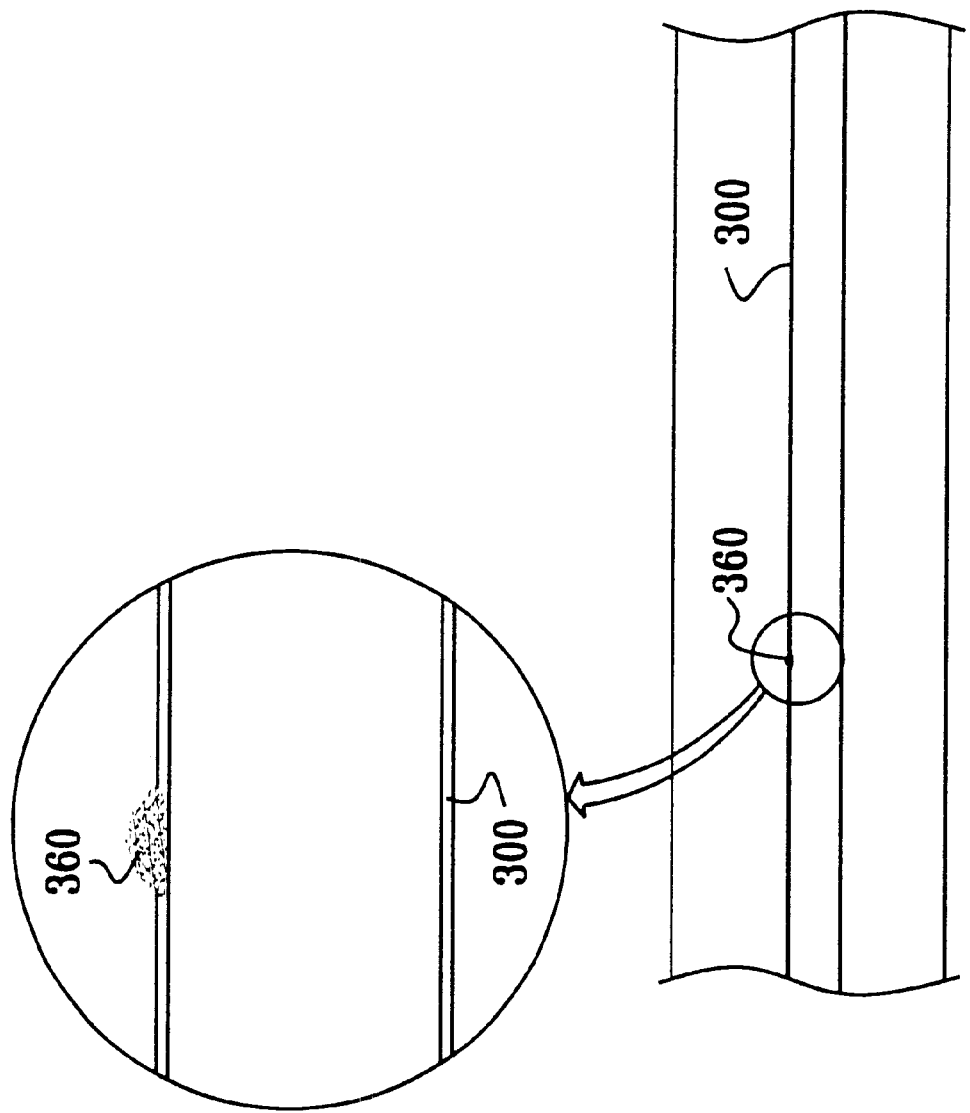

Thereafter, the hemostasis device 100 is entirely withdrawn from the patient, leaving a region 360 of hemostasis outside of artery 300, as shown in FIG. 3L.

It will be appreciated by persons skilled in the art that the present invention is not limited by what has been particularly shown and described hereinabove. Rather the scope of the present invention includes both combinations and subcombinations of the various features described hereinabove and shown in the drawings as well as modifications and further developments thereof which would occur to a person of ordinary skill in the art upon reading the foregoing description and which are not in the prior art.

What is claimed is:

1. Apparatus for hemostasis of an artery having a puncture after arterial catheterization, the apparatus comprising:
   a hemostasis device including an elongate flexible hollow shaft having an inflatable anchor balloon at a forward end thereof and an inflatable peripheral balloon adjacent said forward end of said flexible hollow shaft,
   said inflatable anchor balloon and said inflatable peripheral balloon are mounted onto said elongate flexible hollow shaft and separately inflatable, dimensions of said balloons being different from each other, said anchor balloon having a cusp-type configuration when inflated.

2. Apparatus for hemostasis according to claim 1 and wherein said flexible hollow shaft comprises a central bore.

3. Apparatus for hemostasis according to claim 2 and wherein said flexible hollow shaft comprises a wall having an asymmetric cross section, including a relatively thick cross sectional region and a relatively thin cross-sectional region.

4. Apparatus for hemostasis according to claim 3 and wherein there is formed in said relatively thick cross sectional region a peripheral bore which extends to an peripheral balloon inflation location exterior of said wall and communicates thereat with an interior of said peripheral balloon.

5. Apparatus for hemostasis according to claim 4 and wherein said central bore extends to an anchor balloon inflation location at which it communicates with an interior of said inflatable anchor balloon.

6. Apparatus for hemostasis according to claim 2 and wherein said central bore extends to an anchor balloon inflation location communicating with an interior of said inflatable anchor balloon.

7. Apparatus for hemostasis according to claim 5 and wherein said anchor balloon and said central bore are configured such that when said anchor balloon is deflated it can be withdrawn into said central bore at said anchor balloon inflation location.

8. Apparatus for hemostasis according to claim 7 and wherein said anchor balloon is configured such that when it is inflated, it extends beyond the end of said flexible hollow shaft.

9. Apparatus for hemostasis according to claim 2 and wherein said anchor balloon and said central bore are configured such that when said anchor balloon is deflated it can be withdrawn into said central bore at said anchor balloon inflation location.

10. Apparatus for hemostasis according to claim 9 and wherein said anchor balloon is configured such that when it is inflated, it extends beyond the end of said flexible hollow shaft.

11. Apparatus for hemostasis according to claim 8 and also comprising a rod which is displaceable longitudinally inside and along said central bore and which extends through said flexible hollow shaft and terminates at a first end in a manually engageable handle portion and at a second end is attached to said anchor balloon.

12. Apparatus for hemostasis according to claim 2 and also comprising a rod which is displaceable longitudinally inside and along said central bore and which extends through said flexible hollow shaft and terminates in a manually engageable handle portion and at a second end is attached to said anchor balloon.

13. Apparatus for hemostasis according to claim 11 and wherein said rod comprises a multistrand cable surrounded by a plastic cylindrical seal and is attached at an extreme end thereof to an inner surface of said anchor balloon.

14. Apparatus for hemostasis according to claim 12 and wherein said rod comprises a multistrand cable surrounded by a plastic cylindrical seal and is attached at an extreme end thereof to an inner surface of said anchor balloon.

15. Apparatus for hemostasis according to claim 13 and also comprising a stopcock and associated conduit, communicating with an interior of a head element to which said flexible hollow shaft is fixed at a rearward end thereof.

16. Apparatus for hemostasis according to claim 15 and wherein said interior of said head element communicates with said central bore of said flexible hollow shaft and thus communicates with said interior of said anchor balloon at said anchor balloon inflation location.

17. Apparatus for hemostasis according to claim 14 and also comprising a stopcock and associated conduit, communicating with an interior of a head element to which said flexible hollow shaft is fixed at a rearward end thereof.

18. Apparatus for hemostasis according to claim 17 and wherein said interior of said head element communicates with said central bore of said flexible hollow shaft and thus communicates with said interior of said anchor balloon at said anchor balloon inflation location.

19. Apparatus for hemostasis according to claim 16 and also comprising a stopcock and associated conduit, communicating with an interior said peripheral bore and thus communicates with the interior of said peripheral balloon.

20. Apparatus for hemostasis according to claim 18 and also comprising a stopcock and associated conduit, communicating with an interior said peripheral bore and thus communicates with the interior of said peripheral balloon.

21. Apparatus for hemostasis of an artery having a puncture after arterial catheterization, the apparatus being adapted for use with a catheter introducer having a forward end and comprising:

a hemostasis device including an elongate flexible hollow shaft having an inflatable anchor balloon at a forward end thereof and an inflatable peripheral balloon adjacent said forward end of said flexible hollow shaft, said inflatable anchor balloon and said inflatable peripheral balloon are mounted onto said elongate flexible hollow shaft and separately inflatable, dimensions of said balloons being different from each other, said anchor balloon having a cusp-type configuration when inflated.

22. Apparatus for hemostasis according to claim 21 and wherein said flexible hollow shaft comprises a central bore.

23. Apparatus for hemostasis according to claim 22 and wherein said flexible hollow shaft comprises a wall having an asymmetric cross section, including a relatively thick cross sectional region and a relatively thin cross-sectional region.

24. Apparatus for hemostasis according to claim 23 and wherein there is formed in said relatively thick cross sectional region a peripheral bore which extends to an peripheral balloon inflation location exterior of said wall and communicates thereat with an interior of said peripheral balloon.

25. Apparatus for hemostasis according to claim 24 and wherein said central bore extends to an anchor balloon inflation location at which it communicates with an interior of said inflatable anchor balloon.

26. Apparatus for hemostasis according to claim 22 and wherein said central bore extends to an anchor balloon inflation location communicating with an interior of said inflatable anchor balloon.

27. Apparatus for hemostasis according to claim 25 and wherein said anchor balloon and said central bore are configured such that when said anchor balloon is deflated it can be withdrawn into said central bore at said anchor balloon inflation location.

28. Apparatus for hemostasis according to claim 27 and wherein said anchor balloon is configured such that when it is inflated, it extends beyond the end of said flexible hollow shaft.

29. Apparatus for hemostasis according to claim 22 and wherein said anchor balloon and said central bore are configured such that when said anchor balloon is deflated it can be withdrawn into said central bore at said anchor balloon inflation location.

30. Apparatus for hemostasis according to claim 29 and wherein said anchor balloon is configured such that when it is inflated, it extends beyond the end of said flexible hollow shaft.

31. Apparatus for hemostasis according to claim 28 and also comprising a rod which is displaceable longitudinally inside and along said central bore and which extends through said flexible hollow shaft and terminates at a first end in a manually engageable handle portion and at a second end is attached to said anchor balloon.

32. Apparatus for hemostasis according to claim 22 and also comprising a rod which is displaceable longitudinally inside and along said central bore and which extends through said flexible hollow shaft and terminates in a manually engageable handle portion and at a second end is attached to said anchor balloon.

33. Apparatus for hemostasis according to claim 31 and wherein said rod comprises a multistrand cable surrounded by a plastic cylindrical seal and is attached at an extreme end thereof to an inner surface of said anchor balloon.

34. Apparatus for hemostasis according to claim 32 and wherein said rod comprises a multistrand cable surrounded by a plastic cylindrical seal and is attached at an extreme end thereof to an inner surface of said anchor balloon.

35. Apparatus for hemostasis according to claim 33 and also comprising a stopcock and associated conduit, communicating with an interior of a head element to which said flexible hollow shaft is fixed at a rearward end thereof.

36. Apparatus for hemostasis according to claim 35 and wherein said interior of said head element communicates with said central bore of said flexible hollow shaft and thus communicates with said interior of said anchor balloon at said anchor balloon inflation location.

37. Apparatus for hemostasis according to claim 34 and also comprising a stopcock and associated conduit, communicating with an interior of a head element to which said flexible hollow shaft is fixed at a rearward end thereof.

38. Apparatus for hemostasis according to claim 37 and wherein said interior of said head element communicates with said central bore of said flexible hollow shaft and thus communicates with said interior of said anchor balloon at said anchor balloon inflation location.

39. Apparatus for hemostasis according to claim 36 and also comprising a stopcock and associated conduit, communicating with an interior said peripheral bore and thus communicates with the interior of said peripheral balloon.

40. Apparatus for hemostasis according to claim 38 and also comprising a stopcock and associated conduit, communicating with an interior said peripheral bore and thus communicates with the interior of said peripheral balloon.

* * * * *